(12) United States Patent
Saadat (10) Patent No.: US 7,753,853 B2
(45) Date of Patent: Jul. 13, 2010

(54) LEFT ATRIAL ACCESS APPARATUS AND METHODS

(75) Inventor: Vahid Saadat, Saratoga, CA (US)

(73) Assignee: Hansen Medical, Inc., Mountain View, CA (US)

( * ) Notice: Subject to any disclaimer, the term of this patent is extended or adjusted under 35 U.S.C. 154(b) by 79 days.

(21) Appl. No.: 12/110,585

(22) Filed: Apr. 28, 2008

(65) Prior Publication Data

US 2008/0200821 A1 Aug. 21, 2008

Related U.S. Application Data

(62) Division of application No. 10/949,422, filed on Sep. 24, 2004.

(60) Provisional application No. 60/506,465, filed on Sep. 26, 2003.

(51) Int. Cl.
*A61B 5/00* (2006.01)

(52) U.S. Cl. .................. 600/486; 600/309; 600/323

(58) Field of Classification Search .................. None
See application file for complete search history.

(56) References Cited

U.S. PATENT DOCUMENTS

| | | | |
|---|---|---|---|
| 4,924,877 A | 5/1990 | Brooks | |
| 4,974,929 A | 12/1990 | Curry | |
| 5,465,733 A | 11/1995 | Hinohara et al. | |
| 5,500,012 A | 3/1996 | Brucker et al. | |
| 6,032,059 A | 2/2000 | Henning et al. | |
| 6,058,321 A | 5/2000 | Swayze et al. | |
| 6,241,744 B1 | 6/2001 | Imran et al. | |
| 6,264,611 B1 | 7/2001 | Ishikawa et al. | |
| 6,277,082 B1 | 8/2001 | Gambale | |
| 6,328,699 B1 | 12/2001 | Eigler et al. | |
| 6,398,738 B1 | 6/2002 | Millar | |
| 6,496,738 B2 | 12/2002 | Carr | |
| 6,591,144 B2 * | 7/2003 | Pigott | 607/119 |
| 6,650,923 B1 | 11/2003 | Lesh et al. | |
| 6,770,027 B2 | 8/2004 | Banik et al. | |
| 7,056,294 B2 | 6/2006 | Khairkhahan et al. | |

(Continued)

FOREIGN PATENT DOCUMENTS

WO 01/78596 * 10/2001

(Continued)

OTHER PUBLICATIONS

International Search Report mailed Jan. 20, 2006 for PCT Patent Application No. PCT/US04/31531, filed Sep. 24, 2004, (4 pages).

(Continued)

*Primary Examiner*—Robert L Nasser
(74) *Attorney, Agent, or Firm*—Vista IP Law Group, LLP (57) ABSTRACT

Left atrial access apparatus and methods are described herein. Different parameters, such as oxygen saturation difference, between the left and right atrial chambers is utilized to guide a needle or catheter into a desired position within the heart. Various sensing elements can be utilized to detect the physiological parameter difference, such as oxygen levels, in the left atrium. The sensor can be carried by the needle, at its tip or along its body, and can measure the physiological parameter levels contained in the blood, fluid, or tissue.

13 Claims, 5 Drawing Sheets

U.S. PATENT DOCUMENTS

| | | | |
|---|---|---|---|
| 2002/0128570 A1* | 9/2002 | Bowman et al. | 600/567 |
| 2003/0135124 A1* | 7/2003 | Russell | 600/500 |
| 2003/0195577 A1 | 10/2003 | Pigott | |
| 2004/0143262 A1 | 7/2004 | Visram et al. | |
| 2004/0193147 A1 | 9/2004 | Malecki et al. | |
| 2005/0197530 A1 | 9/2005 | Wallace et al. | |

FOREIGN PATENT DOCUMENTS

| | | | |
|---|---|---|---|
| WO | WO 2004/086944 A2 | 10/2004 | |
| WO | WO 2004/086950 A2 | 10/2004 | |
| WO | WO 2004/086951 A2 | 10/2004 | |
| WO | WO 2004/087235 A2 | 10/2004 | |
| WO | WO 2004/087235 A3 | 10/2004 | |

OTHER PUBLICATIONS

File history for related U.S. Appl. No. 10/949,422, Inventor Vahid Saadat, filed Sep. 24, 2004, including (66 pages total): Final Office Action for U.S. Appl. No. 10/949,422, mailed May 12, 2009; Amendment Response to Non Final Office Action mailed Sep. 2, 2008, for U.S. Appl. No. 10/949,422, submitted on Feb. 2, 2009; Non Final Office Action for U.S. Appl. No. 10/949,422, mailed Sep. 2, 2008; Amendment Response to Final Office Action mailed Mar. 17, 2008 for U.S. Appl. No. 10/949,422, submitted on Jun. 17, 2008; Final Office Action for U.S. Appl. No. 10/949,422, mailed Mar. 17, 2008; Amendment Response to Non Final Office Action mailed Aug. 22, 2007, for U.S. Appl. No. 10/949,422, submitted on Nov. 21, 2007; Non Final Office Action for U.S. Appl. No. 10/949,422, mailed Aug. 22, 2007.

Communication from the European Patent Office, EPO form 1507.4, for related application No. 04789063.7-1265, PCT/US2004031531 with the Supplementary European Search Report and Annex to the European Search Report, Applicant Hansen Medical, Inc., dated May 27, 2009 (3 pages).

Response to Final Office Action dated May 12, 2009 for related U.S. Appl. No. 10/949,422, Inventor Vahid Saadat, filed Sep. 24, 2004, Hansen Medical, Inc. response submitted on Jul. 27, 2009 (12 pages).

* cited by examiner

LEFT ATRIAL ACCESS APPARATUS AND METHODS

RELATED APPLICATION DATA

This application is a divisional of U.S. patent application Ser. No. 10/949,422, filed Sep. 24, 2004, which claims priority to U.S. Ser. No. 60/506,465 filed Sep. 26, 2003, which are incorporated herein by reference in their entirety.

FIELD OF THE INVENTION

The present invention relates generally to medical devices used for detecting parameters within the body. More particularly, the present invention relates to apparatus and methods for facilitating or enabling access across the atrial septum, e.g., for septostomy procedures within the heart.

BACKGROUND OF THE INVENTION

The mammalian heart is divided into four chambers. The superior or upper two chambers include the left and right atria. The right atrium is fluidly in communication with the venous system and carries deoxygenated blood. The left atrium receives oxygenated blood from the lungs and facilitates the movement of this blood into the left ventricle for pumping throughout the body.

The inferior vena cava (IVC) and the superior vena cava (SVC) generally lie, more or less, on a straight line from the diaphragm to the jugular vein. The right atrium forms a chamber that connects the two. Also draining into the right atrium is the coronary sinus. The right atrium lies anteriorly (in front of) and to the right side of the left atrium. The intra-atrial septum is a small area where the two atria are opposed to each other. The diameter of this structure is approximately 30-35 mm in the adult human. The intra-atrial septum is embryologically formed by the fusion of the septum secundum and the septum primum. In approximately 20% of adults, the septum is not fused and a potential passed therebetween exists known as a patent foramen ovale (PFO). Surrounding the intra-atrial septum, outside of the atrial walls, is the pericardial space. Anterior to the right atrium lies the aorta. Posterior to the left atrium lies the pulmonary veins.

For many procedures, e.g., mitral valvuloplasty, left atrial appendage closure, and left-sided arrhythmia ablation, it is desirable to enter or access the left atrium to effect the desired procedure while minimizing trauma to the patient. To non-operatively effect such access, one conventional approach involves puncturing the intra-atrial septum from the right atrial chamber to the left atrial chamber. For emerging procedures such as percutaneous valve repair and replacement, transeptal access to the left atrial chamber of the heart may allow for larger devices to be introduced into the venous system than can generally be introduced percutaneously into the arterial system.

The process of traversing from the right atrium and into the left atrium is called septostomy as the atrial septum is typically penetrated. Septostomy involves direct targeting of a small area of the atrial septum. If the targeted area is missed by the penetrating device, structures such as the aorta or the free wall of the atrium may be in danger of being penetrated. If such a penetration were to occur, serious injury or death to the patient could result. In fact, the most common serious complication of transeptal puncture is cardiac tamponade, a life-threatening condition resulting from misplacement of the transeptal puncture leading to bleeding into the pericardial space.

Interventional cardiologists typically gain access to the left atrium by performing a transeptal puncture using a special needle. The needle, which is hollow, is typically guided by utilizing fluoroscopy. However, fluoroscopy provides only two-dimensional imaging and does not preclude the possibility of the clinician inadvertently puncturing the septum in the wrong location. Some reports have shown that trans-esophageal echocardiography and intracardiac echocardiography can improve the safety of transeptal puncture; however these additional procedures are expensive, inconvenient, and add further risk to the procedure.

Perfecting the technique of transeptal puncture is very challenging for the clinician. Very few interventional cardiologists and electrophysiologists are currently skilled at this procedure. As difficult as it is to perform, it is more difficult to teach and relies upon both visual and tactile senses. Obtaining safe access to the left atrium remains a major obstacle to the growth of the technologies relating to the left atrium, e.g., left-sided arrhythmia mapping and ablation, atrial appendage closure in atrial fibrillation, percutaneous repair and replacement of heart valves, etc.

BRIEF SUMMARY OF THE INVENTION

To gain access to the left atrium within the heart, a transeptal puncture may be performed by a clinician utilizing a sounding procedure. Such a procedure may take advantage of physiological parameter differences between the left and right atrial chambers to detect a direct pathway therebetween. For example, one method may be to utilize the oxygen saturation difference between the atrial chambers in guiding a needle or catheter into the appropriate position.

Generally, an apparatus for detecting a physiological parameter may comprise a probe configured to pierce a tissue region of interest, a sensor disposed near or at the distal end of the probe, the sensor being adapted to detect the physiological parameter, and a guidewire connected to the probe and adapted to advance the sensor towards the tissue region of interest.

A method of locating the tissue region of interest for passage of an apparatus therethrough may also be utilized with any variation of the apparatus where the method generally comprises probing an area of tissue with a probe, sensing a physiological parameter of the tissue while probing the area, and piercing the tissue at least partially with the probe upon detecting a change in the sensed physiological parameter.

The left and right atria carry blood that varies in several parameters. For instance, the left atrium's blood oxygen saturation may reach 99% whereas the right atrium may have an oxygen saturation of only 80% or lower. Moreover, the pressure in the left atrium, except in certain disease states, is typically higher than the pressure in the right atrium. The resulting pressure wave forms have different amplitudes and differ in the atria and other neighboring cardiac structure.

One way to use the oxygen saturation difference between the two chambers in order to guide a needle or catheter into the right position is by using a sensing element to detect the oxygen levels in the left atrium. The sensor may be carried by the needle at its tip or along its body and can be used to measure the level of, e.g., oxygen, carbon dioxide, etc., contained in the blood.

Other variations of the sensor assembly may utilize light reflectance and absorbance differences, as well as various polymeric materials for sensing concentrations of various gases within the blood.

In locating the desired pathway from the right atrium to the left atrium, a needle may be guided to an initial location on the tissue between the atrial chambers. The needle may be penetrated into the tissue to take a measurement of the desired physiological parameter. If an unsuccessful measurement is detected, the needle may be moved to a second location where another measurement may be taken. This process may be repeated any number of times over the tissue region of interest while following a predetermined pattern until a physiological parameter change is detected which is indicative of entry into the left atrium.

DETAILED DESCRIPTION OF THE INVENTION

The left and right atria carry blood that varies in several physiological parameters. For example, the left atrium's blood oxygen saturation may reach 99% whereas the right atrium may only reach an oxygen saturation of 80% or lower. Another parameter includes pressure differences. The pressure in the left atrium is normally higher than the pressure in the right atrium, except in certain disease states. Also, the pressure wave forms have different amplitudes. Moreover, the wave forms also differ between the atria and other neighboring cardiac structures, such as the aorta (which has high velocity blood flow), and the intra-atrial septum or pericardium (which have no blood flow).

To gain access to the left atrium when performing a transeptal puncture, a clinician can perform a sounding procedure by utilizing any of the physiological parameter differences to detect a direct pathway. One method may be to utilize the oxygen saturation difference between the atrial chambers in guiding a needle or catheter into the appropriate position. As shown in the illustrative diagram of mammalian heart H in FIG. 1A, sensor assembly 10 generally comprising a hollow or solid needle 12 and sensing element 14 disposed near or at the distal end of assembly 10 may be passed initially into the right atrium RA, for example, via the inferior vena cava or the superior vena cava. Needle 12 and sensor 14 may be disposed on the distal end of guidewire 16 which provides sufficient flexibility and strength for manipulating the assembly 10 via the proximal end of guidewire 16 located externally of the patient's body. Assembly 10 may be integrated with the guidewire 16 to form a unitary structure. Alternatively, assembly 10 may be fabricated and connected separately to guidewire 16. The guidewire 16 may be a conventional guidewire having a variety of diameters, e.g., 0.35 mm (0.014 in.) or 0.5 mm (0.021 in.) or 0.9 mm (0.035 in.), etc. Right ventricle RV and left ventricle LV are also shown for orientation.

Figure 1A:
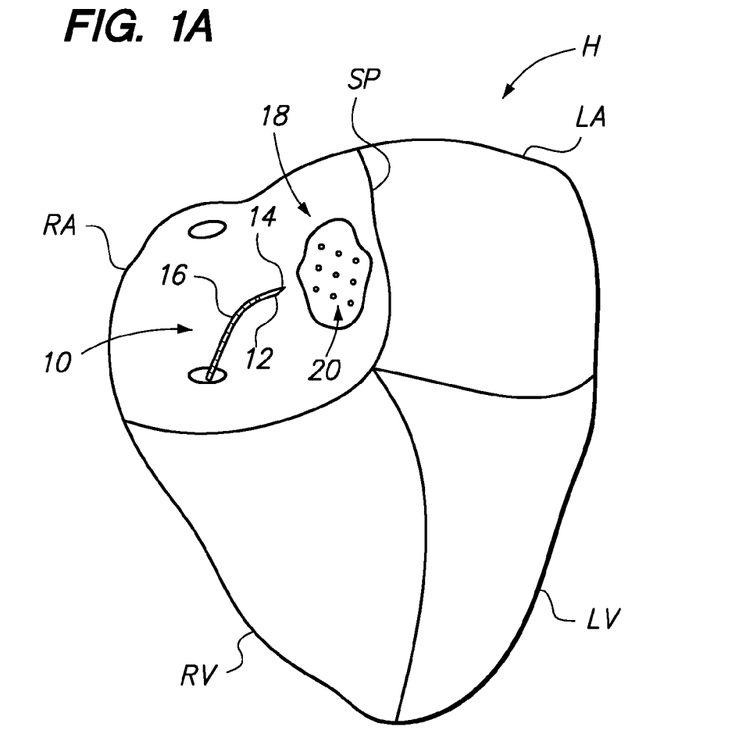
FIG. 1A shows an illustrative diagram of the heart and the atrial septum separating the left atrium and the right atrium with one variation of the sensing apparatus probing the septum.

Sensor 14 may be used to detect the physiological parameter, in this example oxygen levels, in the right atrium RA. Needle 12 and sensor 14 may then be pressed against or passed into or through the septum SP to take an additional measurement of the tissue or fluid environment beyond septum SP. A number of measurements 20 may be performed over an area of tissue 18 over septum SP likely to lead directly to the left atrium LA. In this example, sensor 14 may be carried by needle 12 at the tip or along the needle body, as described below in further detail. Sensor 14 may be used to measure the level of oxygen or carbon dioxide contained in the tissue or blood within which sensor 14 is positioned. As needle 12 penetrates the septum SP and enters into the left atrium LA, the sensed oxygen saturation will change from venous blood to tissue and then to arterial blood having a relatively higher degree of oxygen saturation. This rise in the sensed oxygen level is an indication that a path to the left atrium LA has been located.

Figure 1B:
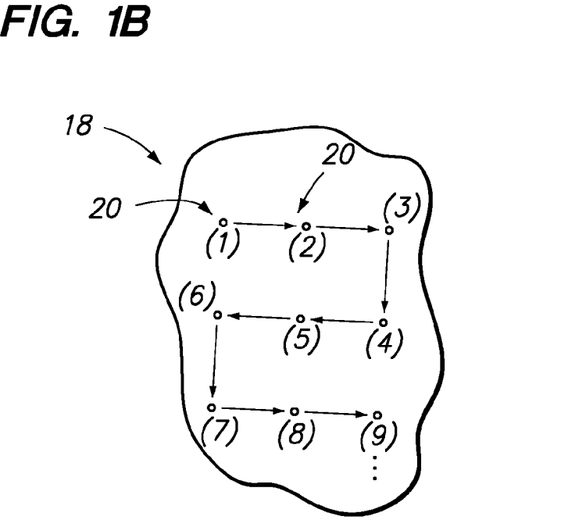
FIG. 1B shows a detailed view of the probed area of the atrial septum and one example of a pattern that may be implemented by the sensing apparatus for detecting the septum for accessing the left atrium.

The needle 12 used may be relatively small in thickness, e.g., about 20-27 gauge, so that the clinician can repeatedly probe the tissue area of interest 18 that is thought to be the true septum SP separating the right atrium RA and the left atrium LA without fear of causing permanent damage to the tissue. A beveled needle 12 will normally leave a slit-like track through the tissue that automatically seals after the needle 12 is retracted from the tissue. In probing the tissue region of interest 18, needle 12 may be guided to an initial location, point 1, where needle 12 may be inserted into the tissue to penetrate the septum SP to take a measurement 20 of the physiological parameter. If an unsuccessful measurement is detected, needle 12 may be moved to a second location, point 2, where another measurement may be taken. This process may be repeated any number of times over the tissue region of interest 18 while following a predetermined pattern, e.g., taking measurements from point 1 to point n, as shown in the detail view of FIG. 1B, until a physiological parameter change is detected which is indicative of entry into the left atrium LA.

Figure 2A:
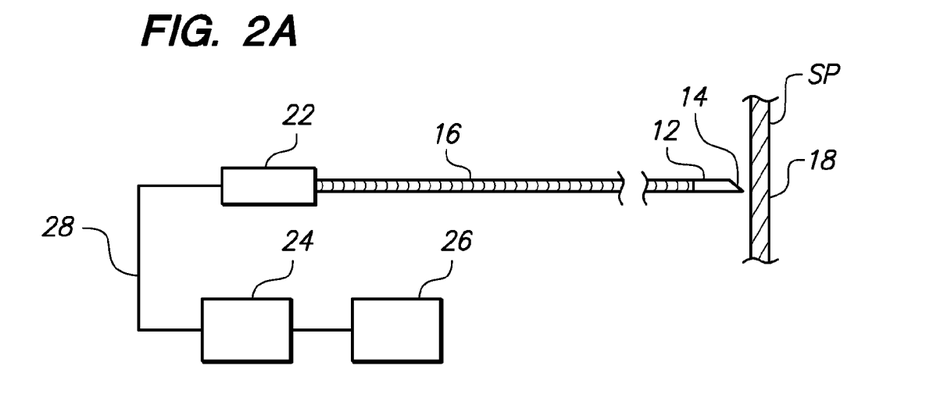
FIGS. 2A to 2C respectively illustrate one example of how a sensing apparatus may be utilized to probe the atrial septum, and once a favorable location is detected, how the sensing apparatus may be advanced through the septum so that another therapeutic device, such as a catheter, may be advanced over the sensing apparatus and into the newly created opening for effecting treatment within the left atrium.

FIG. 2A shows an illustrative assembly side view of needle 12 and sensor 14 disposed on the distal end of guidewire 16. In this variation, the proximal end of guidewire 16 may have handle 22 optionally mounted thereto to facilitate handling and manipulation of guidewire 16 and needle 12 within the body. Sensor 14 located near or at the distal end of needle 12, may be electrically connected, e.g., via conductive wire(s) 28, through guidewire 16 to a detector unit 24 which can be used to receive and process the sensed parameters from sensor 14. Detector 24 may be further in electrical communication with user interface or display 26 which may be used to present or indicate the sensed measurements to the clinician.

Figure 2B:
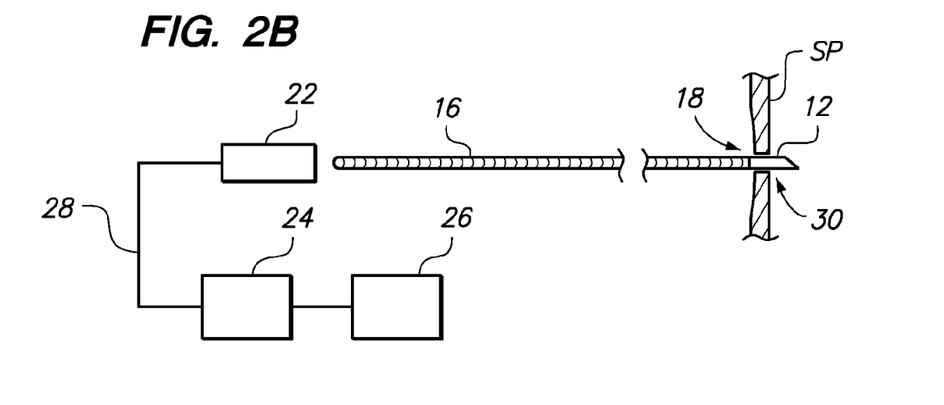
Figure 2C:
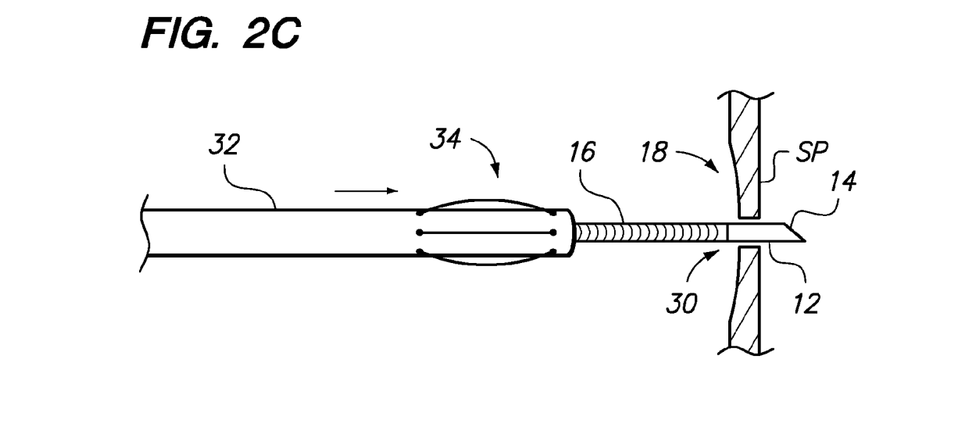

As mentioned above, sensor 14 positioned on needle 12 can detect one of a number of parameters, e.g., oxygen saturation, temperature, carbon dioxide concentration, blood pressure, blood velocity, pH, etc. If the sensed parameter is of sufficient nature indicating the left atrium LA has been penetrated through a newly created opening 30, as shown in FIG. 2B, then the handle 22 (if used) located on the proximal portion of guidewire 16 may be removed. Once handle 22 has been removed, any number of catheter devices 32, such as a dilator or a therapeutic catheter or any number of catheters having a desired end effector 34, may be advanced over guidewire 16 and into the left atrium LA through the opening 30 created by needle 12, as shown in FIG. 2C.

In an alternative variation, robotically-controlled catheters may be used to perform a raster scan to detect the proper pathway to the left atrium LA. A robotically guided needle system may offer an advantage of avoiding a previously tested area by tracking the needle's current and previously probed areas within the target region 18.

In an alternative variation, a tapered and curved dilator and sheath about 68 cm, for instance, similar to a "Mullens" sheath having a 0.8 mm lumen (0.032 in), may be placed into the superior vena cava over a guidewire using fluoroscopic guidance. The guidewire may be removed from the patient and a sensing needle 12 (which can be placed within a second hollow puncturing needle) may then be advanced to a position just inside the tip of the dilator. This needle 12 can be connected electrically to a detector 24 outside the patient and a physiological parameter of the environment around the needle tip 12 can be measured. This parameter measurement can be continuous or intermittent depending upon the desired results. While this parameter is being measured, the needle 12 may be withdrawn under fluoroscopic guidance and positioned in the vicinity of the intra-atrial septum SP. The needle 12 may then be advanced to penetrate into the septum SP with the goal of finding the left atrium LA.

The milieu or parameter sensor 14 can be made in various ways for measuring the local milieu of the environment it is placed within. Described below are examples of variations of sensors 14 which may be utilized. However, these examples are intended to be illustrative and are not intended to limit the scope of the types of sensors and needles described herein. Furthermore, it is also intended that any combination of these sensors can also be used to acquire multiple parameters from the local area.

Figure 3A:
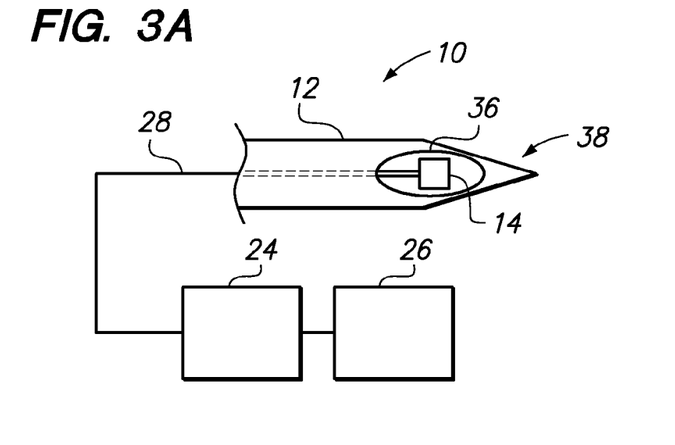
FIGS. 3A and 3B show top and side views, respectively, of one variation of the sensing apparatus in a hollow needle incorporating an integrated sensor at its tip.
Figure 3B:
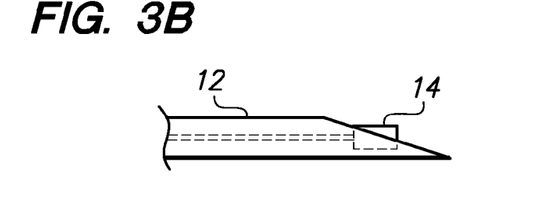

FIGS. 3A and 3B show illustrative top and side views, respectively, of one variation of sensor assembly 10. As shown, needle 12, which may be hollow or solid, may incorporate an integrated sensor 14 near or at its tip 38. Sensor 14 is shown in this example as being positioned within needle opening or port 36. Sensor 14 may also be utilized as a transducer and convert the sensed physiological parameter acquired from the environment into an electric signal. The sensed parameters and/or electrical signals may be transmitted via electrical connection 28 to detector 24, which may be located externally of the patient. As described above, sensor 14 may be configured to be a temperature sensor, a light-emitting device in addition to a photodiode for detecting the same, an ultrasound sensor, a pH sensor, an antenna, etc., or any combination thereof.

Sensor 14, for instance, may be an ultrasound crystal which changes its resonance as a function of the tissue or fluid the crystal is placed within. Blood and cardiac tissue will generate a different response each. By measuring the resonance of the sensor or transducer 14, a clinician can assess whether the needle 12 and sensor 14 is located within the tissue wall or within the flowing blood environment.

Figure 4:
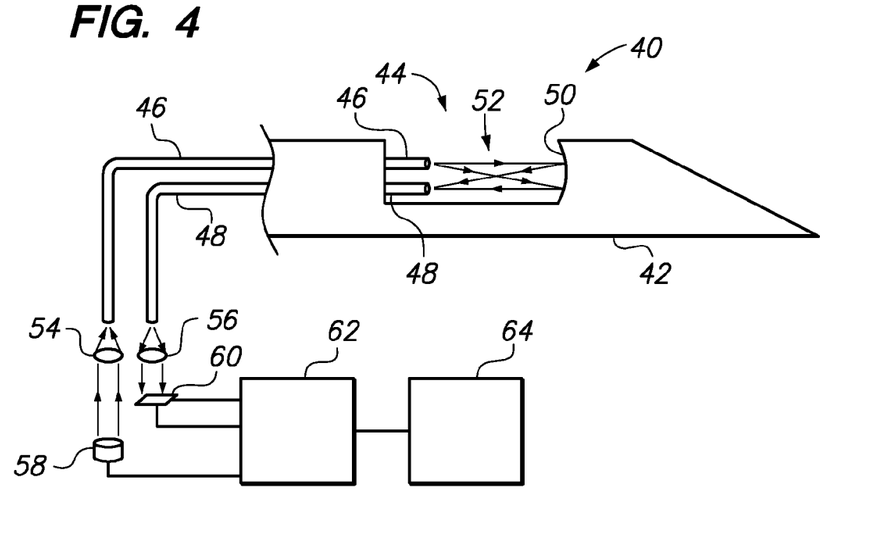
FIG. 4 shows a detailed side view of another variation of the sensing apparatus utilizing reflective fiberoptic transducers for detecting physiologic parameters in probing the atrial septum.

FIG. 4 shows an illustrative side view of another sensor variation 40. This particular sensor assembly 40 shows a reflective type measurement device in which one or more light signals are passed to the tip of the needle 42 via a transmitter optical fiber 46. The light signal may be generated by a light source 58 located outside the body and passed through one or more lenses 54 prior to entering transmitter fiber 46. This light signal may pass through a medium, e.g., tissue, fluid, blood, etc., contained between the end of the optical fiber 46 and the reflector 50 within an opening or window defined along needle 42.

In case the tip of the needle 42 is inserted into a blood-containing environment, the light 52 passes through the blood. Once the light hits the reflector 50, it is reflected back on to the receiving optical fiber 48 and transmitted proximally back to detector circuitry 62 located outside the body. One or more lenses 56 may be utilized to filter the reflected light signals, if desired, prior to receiving the reflected light on detector 60. The detector circuitry 62 will then detect the amplitude of the reflected light. By varying the wavelength of the transmitted light and measuring the amplitude of the reflected light, a spectroscopic measurement can be performed and, e.g., the oxygen saturation, carbon dioxide concentration, etc. can be measured and ultimately displayed via display 64 to the clinician.

Figure 5:
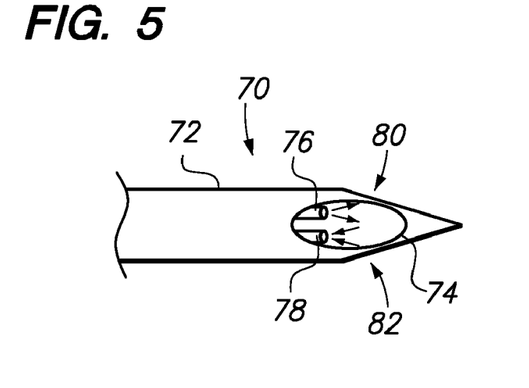
FIG. 5 shows a top view of another variation utilizing reflection of light in the form of scattered back-reflection from surrounding blood or fluids.

FIG. 5 shows a variation of the sensor assembly 70 which is similar to the assembly 40 shown above in FIG. 4. Sensor assembly 70 may utilize the same technique of measuring the light reflection but without the use of a reflector in this instance. Transmitting optical fiber 76 and receiving optical fiber 78 may simply be disposed within an opening 74 defined in needle 72 and the surrounding blood or tissue itself may be utilized to reflect the transmitted light 80 back to receiving optical fiber 78 in the form of scattered back-reflection 82. The backscatter can be measured for amplitude and wavelength to assess, e.g., the oxygen saturation or carbon dioxide concentration.

Figure 6:
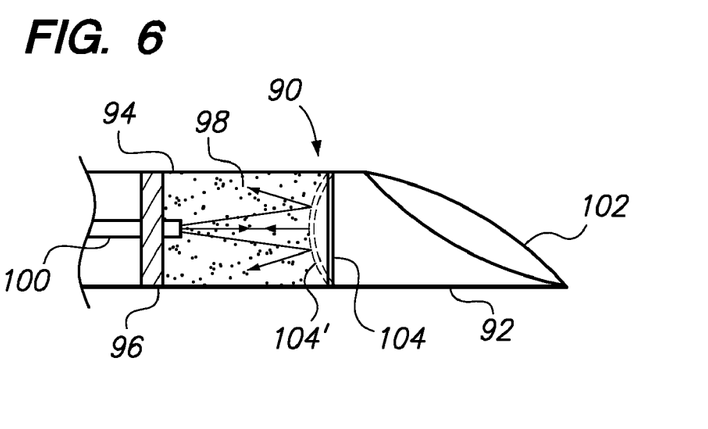
FIG. 6 shows a partial cross-sectional side view of yet another variation utilizing a movable reflective membrane or diaphragm to detect pressure changes.

FIG. 6 shows yet another variation on sensor assembly 90 in a partial cross-sectional side view. In this variation, a pressure transducer may be utilized for detecting absolute or gauge pressure within the atrium as a physiological parameter. Reflective membrane 104 may be disposed within needle body 92 proximally of needle opening 102, which is open to the surrounding environment. As needle 92 is positioned within the atrial chambers, reflective membrane 104 may become displaced 104' in relation to the surrounding pressure. Optical fiber 100 may be positioned proximally of reflective membrane 104 such that the terminal end of fiber 100 is positioned within sensing assembly 94 within needle body 92. A compressed gas, which may have a pressure of about 1 atm (760 mmHg), may fill sensing chamber 98 located between barrier 96 and reflective membrane 104.

Upon being placed in an environment with a higher pressure than the compressed gas within chamber 98, reflective membrane 104' may be displaced accordingly. Optical fiber 100 may emit, as well as receive a reflected light which will re-enter the optical fiber 100. Depending upon the amount of displacement reflective membrane 104' undergoes, a lower amplitude of reflected light will be detected which in turn can be correlated with the outside or detected pressure. A high detected pressure, for example, greater than 50 mmHg, will indicate aortic perforation, while a pressure in the range of, e.g., 15-30 mmHg, is more indicative of the pressure within the left atrium LA.

Figure 7:
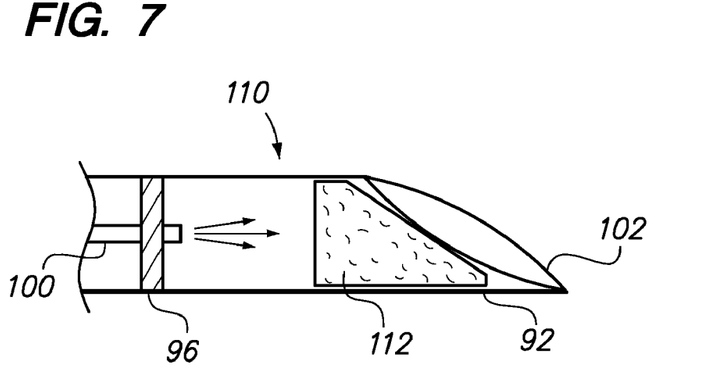
FIG. 7 shows a partial cross-sectional side view of yet another variation utilizing a polymeric material sensitive to oxygen or carbon dioxide concentrations.

FIG. 7 shows yet another variation of sensing assembly 110. In this variation, a polymeric material 112 which is sensitive to oxygen or carbon dioxide concentration, may be positioned within opening 102 within needle 92. As polymer 112 comes into contact with the surrounding blood, polymer 112 may fluoresce according to the gas concentration detected within the blood. Optical fiber 100 positioned proximally or adjacent to polymeric material 112 may be used to measure the fluorescence quenching times which can be utilized in turn to assess the degree of oxygen saturation or carbon dioxide presence. Polymeric materials suitable for such applications are typically found and commercialized by Luxtron Corporation (Santa Clara, Calif.).

Figure 8:
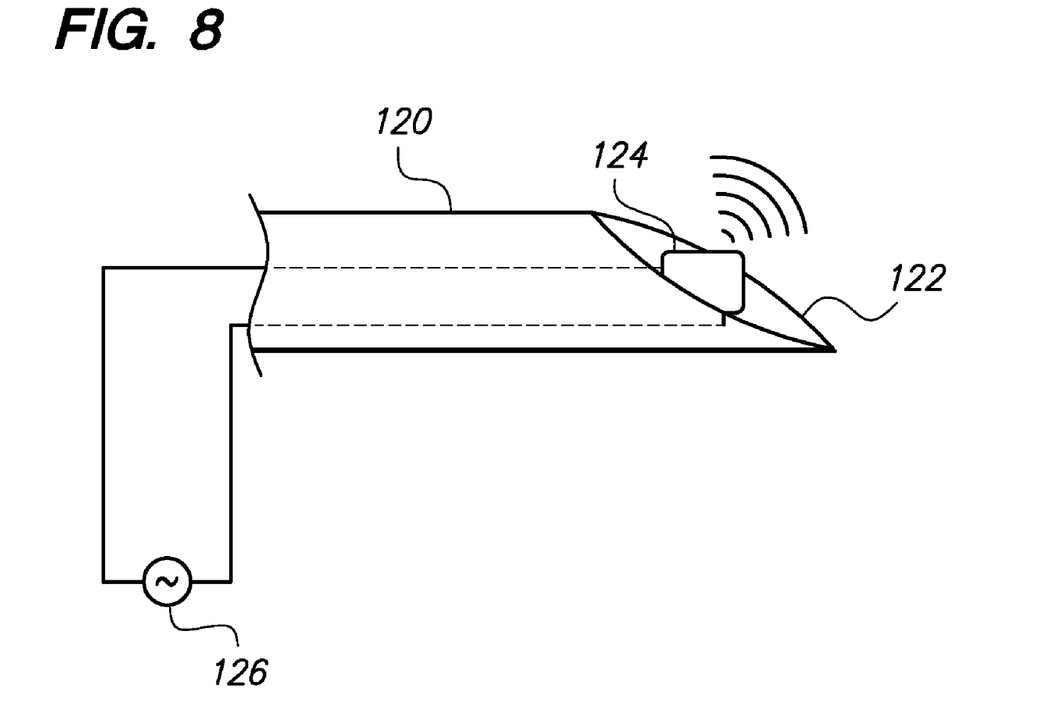
FIG. 8 shows a side view of another variation of the device optionally utilizing a piezo-crystal transducer for detecting the surrounding environment.

An additional parameter such as the resonance of the needle tip can be utilized to ensure that the sensor assembly is not positioned within solid tissue having high oxygen saturation. Such tissue can be found in the walls of the aorta, atrium, and other cardiac structures. For instance, blood velocity may also be measured by an ultrasound crystal in conjunction with another physiological parameter. FIG. 8 shows a side view of a piezo-type crystal transducer 124 positioned within an opening 122 defined within needle 120 and driven by driver 126, which may be located outside the patient body. Such a transducer 124 may be found, e.g., in Doppler systems manufactured by Cardiometrics Inc. (Mountain View, Calif.).

The transducer 124 can emit a pulse of sound energy at ultrasonic frequencies. The reflected sound waves from the immediate environment can indicate whether the area is static (such as in the middle of flesh) or moving (such as in a pool of blood in the left atrium LA). The velocity of blood can indicate a low velocity environment such as the left atrial LA area or a high velocity area such as the aorta, therefore warning against subsequent penetration with a larger catheter. Once it is positively established that the tip of needle 120 is in the left atrium LA, further procedures as described above may be accomplished.

The applications of the disclosed invention discussed above are not limited to certain treatments or regions of the body, but may include any number of other treatments and areas of the body. Modification of the above-described methods for carrying out the invention, and variations of aspects of the invention that are obvious to those of skill in the arts are intended to be within the scope of this disclosure. Moreover, various combinations of aspects between examples is also contemplated and is considered to be within the scope of this disclosure as well.

What is claimed is:

1. A method of locating a tissue region of interest for passage of an apparatus therethrough, comprising:
   advancing the probe to a tissue region of interest within a mammalian heart;
   after advancing the probe to the tissue region of interest, probing an area of tissue with a probe comprising a needle having a sensing element disposed at a distal end thereof, said probing comprising inserting the sensing element at least partially into the tissue region;
   sensing a physiological parameter of the tissue while probing the area; and
   completely piercing the tissue with the probe upon detecting a change in the sensed physiological parameter.

2. The method of claim 1 further comprising advancing the probe into a right atrial chamber of a heart prior to probing an area.

3. The method of claim 1 wherein probing an area of tissue comprises probing the tissue in a predetermined pattern.

4. The method of claim 1 wherein probing an area of tissue comprises probing an atrial septum.

5. The method of claim 1 wherein sensing a physiological parameter comprises sensing the parameter selected from the group consisting of oxygen saturation, temperature, carbon dioxide concentration, blood pressure, blood velocity, pH, and combinations thereof.

6. The method of claim 1 wherein sensing a physiological parameter comprises transmitting a light and measuring its reflectance as being indicative of the physiological parameter.

7. The method of claim 1 wherein sensing a physiological parameter comprises comparing a measurement from the probed area to a measurement from an area proximal of the probed area.

8. The method of claim 1 wherein piercing the tissue comprises advancing the probe into a left atrial chamber.

9. The method of claim 1, wherein the needle comprises a beveled needle sized within the range of 20-27 gauge.

10. The method of claim 1, wherein the probe is robotically guided.

11. A method of locating a tissue region of interest for passage of an apparatus therethrough, comprising:
    probing an area of tissue with a probe comprising a needle having a sensing element disposed at a distal end thereof, said probing comprising inserting the sensing element at least partially into the tissue region;
    sensing a physiological parameter of the tissue while probing the area;
    completely piercing the tissue with the probe upon detecting a change in the sensed physiological parameter; and
    advancing a catheter over a guidewire towards the tissue region of interest, the guidewire being attached to a proximal end of the probe.

12. A method of locating a tissue region of interest for passage of an apparatus therethrough, comprising:
    probing an area of tissue with a probe comprising a needle having a sensing element disposed at a distal end thereof, said probing comprising inserting the sensing element at least partially into the tissue region;
    sensing a physiological parameter of the tissue while probing the area; and
    completely piercing the tissue with the probe upon detecting a change in the sensed physiological parameter,
    wherein sensing a physiological parameter comprises comparing a measurement from a left atrial chamber to a measurement from a right atrial chamber.

13. A method of locating a tissue region of interest for passage of an apparatus therethrough, comprising:
    probing an area of tissue with a probe comprising a needle having a sensing element disposed at a distal end thereof, said probing comprising inserting the sensing element at least partially into the tissue region;
    sensing a physiological parameter of the tissue while probing the area; and
    completely piercing the tissue with the probe upon detecting a change in the sensed physiological parameter,
    wherein the probe is robotically guided with a raster scan.

* * * * *